(12) United States Patent
Fawzy et al.

(10) Patent No.: US 9,775,791 B2
(45) Date of Patent: *Oct. 3, 2017

(54) METHOD OF MANUFACTURE OF ANTIPERSPIRANT SALTS

(71) Applicant: Conopco, Inc., Englewood Cliffs, NJ (US)

(72) Inventors: Karim Mohamed Anwar M Fawzy, Lisburn (GB); Kevin Ronald Franklin, Wirral (GB); Philip Christopher Waterfield, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/889,863

(22) PCT Filed: May 9, 2014

(86) PCT No.: PCT/EP2014/059582
§ 371 (c)(1),
(2) Date: Nov. 9, 2015

(87) PCT Pub. No.: WO2014/187684
PCT Pub. Date: Nov. 27, 2014

(65) Prior Publication Data
US 2016/0106644 A1    Apr. 21, 2016

(30) Foreign Application Priority Data

May 20, 2013  (EP) ..................................... 13168418

(51) Int. Cl.
*A61K 8/26* (2006.01)
*A61K 8/44* (2006.01)
(Continued)

(52) U.S. Cl.
CPC .................. *A61K 8/26* (2013.01); *A61K 8/19* (2013.01); *A61K 8/44* (2013.01); *A61Q 15/00* (2013.01); *A61K 2800/40* (2013.01)

(58) Field of Classification Search
None
See application file for complete search history.

(56) References Cited

U.S. PATENT DOCUMENTS 4,359,456 A    11/1982  Gosling
4,435,382 A    3/1984   Shin
(Continued)

FOREIGN PATENT DOCUMENTS

EP    0308937    3/1989
EP    0405598    1/1991
(Continued)

OTHER PUBLICATIONS

IPRP2 in PCTEP2014059583 dated Sep. 11, 2015.
(Continued)

*Primary Examiner* — Ernst V Arnold
*Assistant Examiner* — Kyung Sook Chang
(74) *Attorney, Agent, or Firm* — Karen E. Klumas

(57) ABSTRACT

A UHT process for the manufacture of an aqueous antiperspirant composition comprising the steps of: (i) mixing aluminium-containing antiperspirant salt, water soluble calcium salt, amino acid, and water, (ii) heating the mixture to a temperature of greater than 100° C. at a pressure of greater than 1 Bar (100,000 Pa) and (iii) restoring the mixture to ambient temperature and pressure.

13 Claims, 1 Drawing Sheet

(51) Int. Cl.
  *A61K 8/19* (2006.01)
  *A61Q 15/00* (2006.01)

(56) References Cited

U.S. PATENT DOCUMENTS

| | | | |
|---|---|---|---|
| 5,955,065 A | 9/1999 | Thong | |
| 6,042,816 A * | 3/2000 | Shen | A61K 8/19 424/65 |
| 6,911,195 B2 | 6/2005 | Vu | |
| 6,942,850 B2 | 9/2005 | Coe | |
| 7,087,220 B2 | 8/2006 | Li | |
| 7,704,531 B2 | 4/2010 | Tang | |
| 2003/0215399 A1 | 11/2003 | Smith | |
| 2004/0115147 A1 | 6/2004 | Vu | |
| 2005/0163737 A1 | 7/2005 | Lemoine | |
| 2006/0204463 A1 | 9/2006 | Tang | |
| 2006/0222612 A1 | 10/2006 | Ni | |
| 2007/0020211 A1 | 1/2007 | Li | |
| 2007/0196303 A1 | 8/2007 | Li | |
| 2007/0286830 A1 | 12/2007 | Li | |
| 2008/0131354 A1 | 6/2008 | Li | |
| 2010/0303749 A1 | 12/2010 | Pan | |
| 2011/0038823 A1 | 2/2011 | Phipps | |
| 2011/0038902 A1 | 2/2011 | Phipps | |
| 2011/0274637 A1 | 11/2011 | Milardovic | |
| 2014/0178321 A1 | 6/2014 | Banowski | |
| 2014/0301963 A1 | 10/2014 | Claas | |

FOREIGN PATENT DOCUMENTS

| | | |
|---|---|---|
| EP | 1104282 | 6/2001 |
| GB | 2113116 | 8/1983 |
| WO | WO0010512 | 3/2000 |
| WO | WO2008063188 | 5/2008 |
| WO | WO2009044381 | 4/2009 |
| WO | WO2009075678 | 6/2009 |
| WO | WO2009076592 | 6/2009 |
| WO | WO2011016807 | 2/2011 |
| WO | WO2012021356 | 2/2012 |
| WO | WO2012060817 | 5/2012 |
| WO | WO2012061280 | 5/2012 |
| WO | WO2012148480 | 11/2012 |
| WO | WO2012148481 | 11/2012 |
| WO | WO2013158077 | 10/2013 |
| WO | WO2014187684 | 11/2014 |
| WO | WO2014187685 | 11/2014 |

OTHER PUBLICATIONS

IPRP2 in PCTEP2014060306, Sep. 16, 2015.
Laden, Antiperspirants and Deodorants 1999 2nd Edition pp. 96-97.
Search Report in EP13168417, Oct. 31, 2013.
Search Report in EP13168418, Oct. 31, 2013.
Search Report in EP14193902, May 6, 2015.
Search Report in PCTEP2014059582, Oct. 6, 2014.
Search Report in PCTEP2014059583, Oct. 6, 2014.
Search Report in PCTEP2014060306, Oct. 6, 2014.
Written Opinion 1 in PCTEP2014059583, Oct. 6, 2014.
Written Opinion 2 in PCTEP2014059583, Apr. 30, 2015.
Written Opinion 2 in PCTEP2014060306, May 8, 2015.
Written Opinion in EP13168417, Oct. 31, 2013.
Written Opinion in EP13168418, Oct. 31, 2013.
Written Opinion in EP14193902, May 6, 2015.
Written Opinion in PCTEP2014059582, Oct. 6, 2014.
Written Opinion in PCTEP2014060306, Oct. 6, 2014.
Co-pending Application: Applicant: Fawzy et al., U.S. Appl. No. 14/889,866, filed Nov. 9, 2015.
Co-pending Application: Applicant: Fawzy et al., U.S. Appl. No. 14/889,874, filed Nov. 9, 2015.
Search Report & Written Opinion in PCTEP2015074528 dated Jan. 20, 2016.
Search Report & Written Opinion in PCTEP2015074529 dated Dec. 21, 2015.
Search Report & Written Opinion in PCTEP2015076365 dated Feb. 11, 2016.
Pluronic(R) F-127, Newdruginfo.com, dated Jun. 7, 2016.
Written Opinion in PCTEP2015074529, Sep. 6, 2016.

* cited by examiner

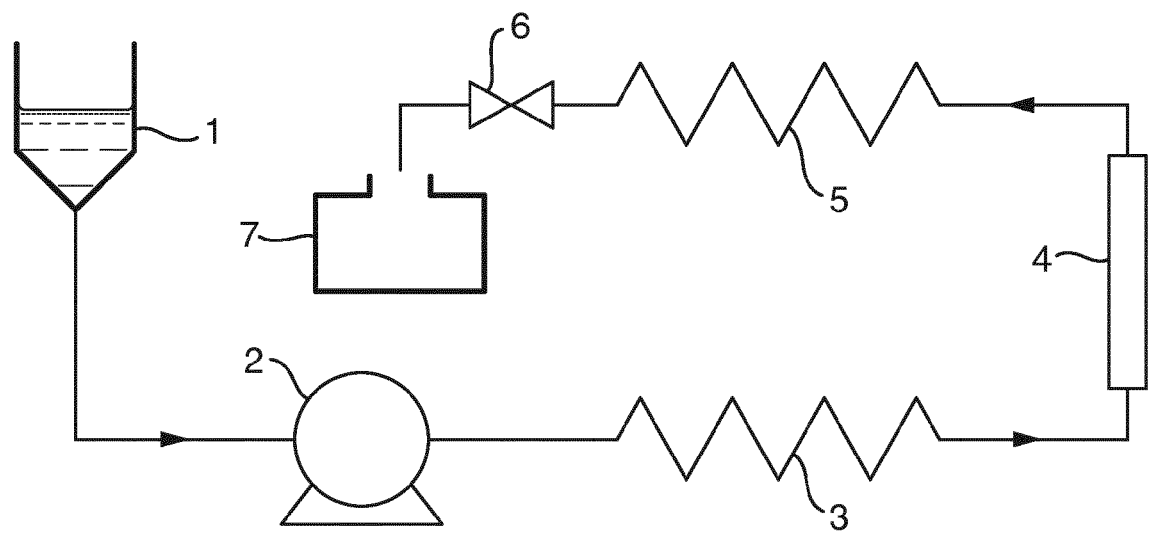

METHOD OF MANUFACTURE OF ANTIPERSPIRANT SALTS

The present invention is concerned with a method of manufacture of antiperspirant salts, particularly aluminium-containing antiperspirant salts having enhanced activity. The invention involves Ultra-High Temperature (UHT) processing of aqueous antiperspirant solutions.

Processes for the manufacture aluminium-containing antiperspirant salts having enhanced activity are well known in the prior art. The antiperspirant salts produced are often described as "activated".

Traditionally, activated antiperspirant salts have been prepared by prolonged heating of basic aluminium chloride solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated antiperspirant salts have also been prepared using water soluble calcium acids, particularly with a further adjunct such as an amino acid, hydroxyl acid, or betaine. Some of these samples could be formulated into aqueous compositions without the antiperspirant losing all of its enhanced activity.

EP 1,104,282 (Gillette) discloses a means of producing activated antiperspirant salts using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate antiperspirant salts and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising aluminium and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining BAC, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

WO 2009/075678, WO 2009/076592, WO 2011/016807, WO 2012/060817, WO 2012/061280, WO 2012/148480 and WO 2012/148481 (Colgate) disclose the manufacture of activated antiperspirant salts by neutralisation of aluminium chloride with calcium hydroxide in the presence of glycine.

The present invention is concerned with the manufacture of antiperspirant salts of enhanced activity and compositions comprising such salts. The salts must be aluminium-containing, which includes aluminium-zirconium salts. The activation process involves the use of a water soluble calcium salt and an amino acid and takes place in aqueous solution at elevated temperature and pressure. The processing involved is frequently referred to as Ultra High Temperature (UHT) processing and has been widely employed in the past in the pasteurisation and sterilisation of milk.

SUMMARY OF THE INVENTION

In a first aspect of the present invention, there is provided a process for the manufacture of an aqueous antiperspirant composition comprising the steps of: (i) mixing aluminium-containing antiperspirant salt, water soluble calcium salt, amino acid, and water, (ii) heating the mixture to a temperature of greater than 100° C. at a pressure of greater than 1 Bar (100,000 Pa) and (iii) restoring the mixture to ambient temperature and pressure.

In a second aspect of the present invention, there is provided an antiperspirant composition manufactured by a process according to the first aspect of the present invention.

In a third aspect of the present invention, there is provided a method of gaining an antiperspirancy benefit comprising the topical application to the surface of the human body of a composition manufactured by a process according to the first aspect of the present invention.

BRIEF DESCRIPTION OF THE DRAWINGS

FIG. 1 is a flow diagram of one embodiment of a process according to the present invention.

The process for the manufacture of an aqueous antiperspirant composition described herein may alternatively be referred to as a process for enhancing the activity or "activating" an antiperspirant salt. It is done by heating the required salt with an amino acid and a water soluble calcium salt at over 100° C. and greater than 1 Bar pressure. We have found that the antiperspirant salt can be activated in a surprisingly short time by use of this process.

The process of the present invention leads antiperspirant compositions delivering surprisingly good antiperspirancy performance. In addition, such compositions have remarkable storage stability, maintaining their good performance for many months.

The activation process is preferably done at over 110° C. At this more elevated temperature, the activation process appears to work quicker and/or produces a more activated product.

It is preferred that the process is done at greater than 2 Bar pressure, particularly when the process is performed at over 110° C. By working at this more elevated pressure, it is possible to work at higher temperatures without loss of the water through boiling off.

The process is preferably performed in a sealed or semi-sealed system. Semi-sealed systems include valved systems in which pressure is released when the system exceeds a particular pressure, this pressure generally being selected by the operator. UHT processing equipment similar to that used in the pasteurisation and sterilization of milk may advantageously be employed.

The aluminium-containing antiperspirant salt is preferably a basic aluminium chlorohydrate (BAC) salt, in particular a salt of general formula $Al_2OH_{6-x}Cl_x$, where is 0.3 to 5, preferably 1 to 2, and more preferably 1 to 1.6. We have found that surprisingly good results are found on using BAC salts commonly referred to as aluminium sesquichlorohydrate (herein ASCH) having the chemical formula $Al_2OH_{4.4}Cl_{1.6}$ to $Al_2OH_{4.9}Cl_{1.1}$. Most commercial ASCH samples are of chemical formula $Al_2OH_{4.7}Cl_{1.3}$ to $Al_2OH_{4.9}Cl_{1.1}$ and it is especially preferred to use BAC salts of this formula.

The aluminium-containing antiperspirant salt used in the present invention preferably has an aluminium to chloride molar ratio of from 1:1 to 2:1, more preferably 1.25:1 to 2:1, and most preferably 1.25:1 to 1.82:1.

The concentration of aluminium used in the process is preferably from 0.5 to 5 mol·dm$^{-3}$ and more preferably from 1.4 to 5 mol·dm$^{-3}$. In certain preferred embodiments, the concentration of aluminium may be over 3 mol·dm$^{-3}$, particularly 3 to 4.5 mol·dm$^{-3}$.

In order for the antiperspirant to become activated, it is important to have sufficient calcium present relative to the amount of aluminium present. The molar ratio of calcium to aluminium is preferably at least 1:40, more preferably at least 1:30 and most preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar rations of calcium to aluminium of at least 1:40 and at least 1:20, it is independently preferred that this ratio is no greater than 1:2 and more preferred that it is no greater than 1:5.

A preferred water soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In order for the antiperspirant to become activated, it is important to have sufficient amino acid present relative to the amount of aluminium present. The molar ratio of amino acid to aluminium is preferably at least 1:20, more preferably at least 1:10 and most preferably at least 1:5. It is not advantageous to have the amino acid concentration in excess of the aluminium concentration; hence, the molar amino acid to aluminium is preferably from 1:20 to 1:1, more preferably from 1:10 to 1:1 and most preferably from 1:5 to 1:1.

A preferred amino acid for use in the present invention is glycine.

The presence of both calcium and amino acid is essential for success of the present invention. In preferred embodiments, the molar ratio of calcium to aluminium is preferably at least 1:40 and the molar ratio of amino acid to aluminium is preferably at least 1:20. In particularly preferred embodiments the molar ratio of calcium to aluminium is at least 1:20 and the molar ratio of amino acid to aluminium is at least 1:10. In especially preferred embodiments the molar ratio of calcium to aluminium is from 1:20 to 1:5 and the molar ratio of amino acid to aluminium is from 1:10 to 1:1.

UHT equipment is commonly used to perform the process of the present invention. Such equipment typically comprises an in feed for the components to be processed, herein "the mixture", a pump, preferably of adjustable speed setting, a means for heating the mixture to a temperature of greater than 100° C. and a means for holding the mixture at elevated temperature. The UHT equipment also requires a means for keeping the mixture at greater than 1 Bar pressure, this usually being a release valve. The equipment is typically arranged such that the mixture passes through the components as listed in the order as listed. The means for heating the mixture to a temperature of greater than 100° C. is typically a heat exchanger, usually of the plate variety. Following its passage through the temperature holding means, there may advantageously be a cooling unit for the mixture, typically a second heat exchanger, usually of the plate variety. The mixture is typically released from the UHT equipment through a pressure release valve.

The process of the present invention may involve pre-mixing of the aluminium-containing antiperspirant salt, water soluble calcium salt, amino acid, and water. This may take place in a pre-mixing vessel before the pre-mix is passed into UHT equipment. In other embodiments, the mixing of these components may be performed within UHT equipment. In these latter embodiments, the UHT equipment used preferably has a homogeniser located in the equipment in such a position that the mixture is homogenised before it is heated.

The mixture exiting the UHT equipment may be placed in a storage tank or it may be pumped directly into a secondary processing unit. Secondary processing of the UHT treated mixture may involve its formulation into an antiperspirant composition by means known in the art. The process of the present invention is particularly suitable for use with secondary processing leading to aqueous antiperspirant compositions, especially those suitable for application from roll-on applicators.

When the mixture exiting the UHT equipment is pumped directly into a secondary processing unit, this may be done with other components intended for the formation of an antiperspirant composition. Such components, in particular any additional water, may serve to cool the mixture to a temperature suitable for further processing. This variant on the processing method optimises heat energy usage. Processes of the type referred to in this paragraph may be described as processes according to the first aspect of the invention, wherein the mixture is further processed with additional components required for the formation of an antiperspirant roll-on composition before the mixture is fully restored to ambient temperature. The further components required for the formation of an antiperspirant roll-on composition typically comprise fragrance and an emulsifier. They may also include the components referred to below as further components generally added to compositions suitable for application from roll-on applicators.

The water soluble "further components" required for the formation of an antiperspirant roll-on composition may be added before or after the activation of the ASCH. That is to say, they may be added as part of the initial pre-mix prior to UHT processing or they may be added thereafter in a secondary processing stage in a secondary processing unit.

Many aspects of the present invention involve secondary processing leading to aqueous antiperspirant compositions, especially those suitable for application from roll-on applicators. Such compositions generally involve the addition of further components as described hereinbelow.

Herein, amounts and concentrations of ingredients are percentages by weight of the total composition, unless otherwise indicated and ratios are ratios by weight.

A preferred additional component of compositions of the invention is an oil.

Herein, the terms "oil" and signifies a water-insoluble organic material that is liquid at 20° C. Any material having a solubility of less than 0.1 g/100 g at 20° C. is considered to be insoluble.

Herein "aqueous compositions" are compositions having a continuous phase that is predominately water; that is to say, greater than 50% water.

A preferred oil for use in compositions prepared in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of oil in the composition is preferably from 0.1 to 20%, more preferably from 0.5 to 10%, and most preferably at from 2 to 8% by weight of the total composition. In certain preferred embodiments, particularly those also comprising an aluminium and/or zirconium containing antiperspirant active, the oil is present at greater than 2.5% and less than 6% by weight of the total composition.

In certain embodiments, it is preferred to include an oil, other than a fragrance oil, that has a relatively low viscosity, by which is meant less 250 cS ($mm^2 \cdot s^{-1}$). Such oils can improve the sensory properties of the composition on application and can lead to other benefits such as emolliency.

Suitable oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable oils can include those derived from unsaturated $C_{18}$ acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable oils comprises non-volatile dimethicones, often comprising phenyl or diphenylene substitution, for example Dow Corning 200 350 cps or Dow Corning 556.

A preferred component in many aqueous antiperspirant compositions prepared in accordance with the invention is an emulsifier. Emulsifiers are particularly advantageous in aqueous systems additionally comprising fragrance oil and/or other oil.

It is preferred that emulsifiers used in the present invention form a lamellar phase emulsifier system in the composition. Such systems may be readily identified by means of optical microscopy. Such systems lead to good emulsion stability in compositions according to the invention.

It is preferred that aqueous antiperspirant compositions prepared in accordance with the present invention comprise a non-ionic emulsifier system. Such an emulsifier system conveniently has a mean HLB value in the region of from about 5 to about 12 and particularly from 6 to about 10. In the preferred embodiments referred to in the paragraph immediately above, an especially desired mean HLB value is from 6 to 9. Such a mean HLB value can be provided by selecting an emulsifier having such an HLB value, or more preferably by employing a combination of at least two emulsifiers, a first (lower) HLB emulsifier having an HLB value in the range of from 2 to 6.5, such as in particular from 4 to 6 and a second (higher) HLB emulsifier having an HLB value in the range of from about 6.5 to 18 and especially from about 12 to about 18. When a combination of emulsifiers is employed, the average HLB value can be calculated as a weight average of the HLB values of the constituent emulsifiers.

Lamellar phase emulsifier systems preferably comprise two non-ionic surfactants, optionally selected as suggested in the paragraph immediately above. In a particular embodiment a first emulsifier is a fatty alcohol, such as cetyl and/or stearyl alcohol and a second emulsifier is much more hydrophilic, having a HLB of from about 6.5 to 18 and especially from about 12 to about 18.

An especially desirable range of emulsifiers comprises a hydrophilic moiety provided by a polyalkylene oxide (polyglycol), and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol. A preferred range of emulsifiers comprises polyethylene glycol ethers.

Preferably the hydrophobic aliphatic substituent contains at least 12 carbons, and is derivable from lauryl, palmityl, cetyl, stearyl, and behenyl alcohol, and especially cetyl, stearyl or a mixture of cetyl and stearyl alcohols or from the corresponding carboxylic acids.

The polyalkylene oxide is often selected from polyethylene oxide and polypropylene oxide or a copolymer of ethylene oxide and especially comprises a polyethylene oxide. The number of alkylene oxide and especially of ethoxylate units within suitable emulsifiers is often selected within the range of from 2 to 100. Emulsifiers with a mean number of ethoxylate units in the region of 2 can provide a lower HLB value of below 6.5 and those having at least 4 such units provide a higher HLB value of above 6.5 and especially those containing at least 10 ethoxylate units which provide an HLB value of above 10. A preferred combination comprises a mixture of an ethoxylate containing 2 units and one containing from 10 to 40 units, such as from 15 to 30 or desirably from 20 to 25. Particularly conveniently, the combination of emulsifiers comprises steareth-2 and a selection from steareth-15 to steareth-30.

It is desirable to employ a mixture of ethoxylated alcohol emulsifiers in a weight ratio of emulsifier having a lower HLB value of less than 6.5 to emulsifier having a higher HLB value of greater than 8 of from 2:1 to 6:1 and particularly from 4:1 to 6:1.

The total proportion of emulsifiers in the composition is usually at least 1% and particularly at least 2% by weight.

Commonly, the emulsifiers are not present at above 10%, often not more than 7% by weight and in many preferred embodiments up to 6% by weight. An especially desirable concentration range for the emulsifiers is from 2.5 to 5% by weight.

Other components that may be present include short chain ($C_2$-$C_4$) alcohols and especially polyols such glycerol, ethylene glycol, propylene glycol and polymers thereof, in particular poly(ethylene glycol) and poly(propylene glycol). Poly(ethylene glycol) of average molecular weight 200 to 600 is a preferred component. Such components may add to the sensory properties of the composition and, when included, are typically present at from 0.5 to 10% of the total composition.

The aqueous compositions prepared in accordance with the present invention are very suitable for dispensing via a roll-on dispenser, for example any upright dispenser such as described in EP1175165 or an invert dispenser such as described in U.S. Pat. No. 6,511,243 or WO05/007377. Invert indicates that the dispenser stands stably with its dispensing ball below the formulation reservoir. In using such dispensers, the composition is applied by rolling the ball of the dispenser across the skin surface, depositing a film of fluid on the skin. Commonly the dispenser is wiped across the skin between 4 and 10 strokes. Commonly from 0.2 to 0.5 g of the composition is deposited in each armpit per application.

EXAMPLES

A pre-mix having the composition indicated in Table 1 was prepared at ambient temperature by co-dissolving the components with stirring. 10 L of the pre-mix was placed in the feed vessel (1) of an Armfield FT74 UHT processing unit, the Flow Diagram for which is schematically illustrated in FIG. 1. An electric variable pump (2) was then started, the pumping rate being set (at 3.6 L/hr), such that the mixture would have the retention times indicated below in the various sections of the unit. The pump forced the pre-mix into a plate heat exchanger (3), where it was heated to 115° C. for 50 j seconds. The mixture then passed into a holding tube (4), where it was maintained at 115° C. for a further 194 seconds. From the holding tube (4), the mixture passed into a second region (5) of the plate heat exchanger, where it was cooled to 30° C. for 56 seconds. Finally, the mixture exited the UHT processing unit (1) through the back pressure release valve (6) into a collection vessel (7). The internal pressure in the UHT unit was kept at between 3 and 7 Bar throughout the process by means of the pressure release valve (6).

TABLE 1

| Material | Parts by weight |
|---|---|
| Reach 301 powder* | 15 |
| Calcium chloride (anhydrous) | 1.5 |
| Glycine | 4.7 |
| Water | 72.6 |
| TOTAL | 93.8 |

*Approximately 100% ASCH obtained from SummitReheis. Al content measured at 24.1% by weight. The ASCH had an approximate general formula of $Al_2(OH)_{4.8}Cl_{1.2}$ and an Al:Cl ratio of approximately 1.67:1.

The solution of activated ASCH resulting from the above UHT process (Solution 1) was used to prepare an antiperspirant roll-on composition as indicated in Table 2 using the following method.

The sunflower seed oil and Steareth-2 were heated in a beaker to 65-70° C. In a separate beaker, the antiperspirant solution was heated to 50-55° C. with the Steareth-20. The oil phase was then slowly added to the aqueous phase with vigorous stirring. After cooling to 42° C., the fragrance was then added and vigorous stirring continued to give the final composition.

TABLE 2

| Antiperspirant Roll-On Composition (Example 1) | |
|---|---|
| Component: | % w/w |
| Antiperspirant Solution 1 | 93.8 |
| Steareth 20 (1) | 0.9 |
| Steareth 2 (2) | 2.3 |
| Sunflower seed oil (3) | 2.0 |
| Fragrance | 1.0 |

(1). Volpol S20, ex Croda.
(2). Volpol S2A, ex Croda.
(3). Akosun, ex AAK Karlshmans.

An analogous composition to the one described above was also prepared using Chlorohydrol solution, a 50% aluminium chlorohydrate (ACH) commercially available from Summit Labs. (Comparative Example A). The full details of two compositions are shown in Table 3.

TABLE 3

| Antiperspirant Roll-On Composition | | |
|---|---|---|
| | % w/w | |
| Component: | Example 1 | Comparative Example A |
| Activated ASCH | Ca. 15 | — |
| ACH | — | Ca. 15 |
| Calcium chloride | 1.5 | — |
| Glycine | 4.7 | — |
| Steareth 20 (1) | 0.9 | 0.9 |
| Steareth 2 (2) | 2.3 | 2.3 |
| Sunflower seed oil (3) | 2.0 | 2.0 |
| Fragrance | 1.0 | 1.0 |
| Water | To 100 | To 100 |

The antiperspirancy performances of the roll-on compositions of Table 3 were compared in a head-to-head hot room clinical study performed with 30 female volunteers. Test operators applied 0.30 g of Example 1 to one axilla and 0.30 g of Comparative Example A (0.30 g) to the other axilla of each panellist. This was done once each day for three days. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The relative sweat weight reduction (SWR) (Example 1 vs. Comparative Example A) for each panellist was calculated as a percentage (% SWR) and the mean % SWR was calculated according to the method described by Murphy and Levine in "Analysis of Antiperspirant Efficacy Results", *J. Soc. Cosmetic Chemists*, 1991 (May), 42, 167-197.

It was found that Example 1 gave a significantly greater SWR than Comparative Example A (p<0.0006).

In a further experiment, a pre-mix having the concentrated composition indicated in Table 4 was prepared at ambient temperature by co-dissolving the components with stirring. 10 L of this pre-mix was processed using UHT equipment by a method analogous to that used to prepare the activate ASCH solution for Example 1, except that the flow rate was set to 5.4 L/hr., the mixture heated to 120° C. for 33 seconds, held at this temperature for 130 seconds, and the cooling time was 66 seconds.

TABLE 4

| Material | Parts by weight |
| --- | --- |
| Reach 301 (ASCH) powder | 15 |
| Calcium chloride (anhydrous) | 1.5 |
| Glycine | 4.7 |
| Water | 14.3 |
| TOTAL | 35.5 |

The solution of activated ASCH resulting from the above UHT process (Solution 2) was used to prepare an antiperspirant roll-on composition according to Table 5, by use of an analogous method to that used for the preparation of Example 1.

TABLE 5

Antiperspirant Roll-On Composition (Example 2)

| Component: | % w/w |
| --- | --- |
| Antiperspirant Solution 2 | 35.5 |
| Water | 58.3 |
| Steareth 20 (1) | 0.9 |
| Steareth 2 (2) | 2.3 |
| Sunflower seed oil (3) | 2.0 |
| Fragrance | 1.0 |

Example 2 also proved to be a highly efficacious antiperspirant composition, giving a significant greater SWR than Comparative Example A (p<0.0001) in a head-to-head test as previously described.

Further Comparative Examples B and C as indicated in Table 6 were prepared by methods analogous to that used for the preparation of Example 1, but using different antiperspirant salt solutions. Comparative Example B used a solution prepared simply by dissolving 15 parts of Reach 301 powder in 78.9 parts of water at ambient temperature. Comparative Example C used an antiperspirant salt solution prepared in the following manner. 15 parts of Reach 301 powder, 1.5 parts anhydrous calcium chloride and 4.7 parts glycine were combined with 72.6 parts water at room temperature. The resulting solution was heated at 85° C. for 18 hours in a capped glass vessel and was then allowed to cool to ambient temperature.

The antiperspirancy performance of Comparative Examples B and C were compared with that of Comparative Example A in further head-to-head hot room clinical studies as described above.

Comparative Example B, which comprised a non-activated ASCH antiperspirant salt, gave approximately the same SWR as Comparative Example A.

Comparative Example C, which comprised an ASCH heated with glycine and calcium chloride for 18 hours at 85° C., gave a SWR similar to that obtained from Examples 1 and 2, despite the much shorter processing times used in the activation of the antiperspirant salts used in these examples.

TABLE 6

| Component: | % w/w Example: | | | | |
| --- | --- | --- | --- | --- | --- |
| | Comp. A | Comp. B | Comp. C | 1 | 2 |
| ASCH | — | Ca. 15 | Ca. 15 | Ca. 15 | Ca. 15 |
| ACH | Ca. 15 | — | — | — | — |
| Calcium chloride | — | — | 1.5 | 1.5 | 1.5 |
| Glycine | — | — | 4.7 | 4.7 | 4.7 |
| Steareth 20 (1) | 0.9 | 0.9 | 0.9 | 0.9 | 0.9 |
| Steareth 2 (2) | 2.3 | 2.3 | 2.3 | 2.3 | 2.3 |
| Sunflower seed oil (3) | 2.0 | 2.0 | 2.0 | 2.0 | 2.0 |
| Fragrance | 1.0 | 1.0 | 1.0 | 1.0 | 1.0 |
| Water | To 100 | To 100 | To 100 | To 100 | To 100 |

In a further experiment, a pre-mix having the highly concentrated composition indicated in Table 7 was prepared at ambient temperature by co-dissolving the components with stirring. On this occasion, the ASCH used was an aqueous solution comprising approximately 50% ASCH, available from BK Giulini GmbH as Aloxicoll 31 L solution. We measured the Al content of this solution as 11.9% by weight. The ASCH had an approximate general formula of $Al_2(OH)_{4.8}Cl_{1.2}$ and an Al:Cl ratio of approximately 1.67:1.

10 L of the pre-mix was processed using UHT equipment by a method analogous to that used to prepare the activate ASCH solution for Example 1, except that the flow rate was set to 1.8 L/hr., the mixture heated to 135° C. for 99 seconds, held at this temperature for 389 seconds, and the cooling time was 200 seconds.

TABLE 7

| Material | Parts by weight |
| --- | --- |
| Aloxicoll 31L (50% ASCH) | 30 |
| Calcium chloride (anhydrous) | 0.9 |
| Glycine | 2.0 |
| Water | 2.6 |
| TOTAL | 35.5 |

The solution of activated ASCH resulting from the above UHT process (Solution 3) was used to prepare an antiperspirant roll-on composition according to Table 8, by use of an analogous method to that used for the preparation of Example 1.

TABLE 8

Antiperspirant Roll-On Composition (Example 3)

| Component: | % w/w |
| --- | --- |
| Antiperspirant Solution 3 | 35.5 |
| Water | 58.3 |
| Steareth 20 (1) | 0.9 |
| Steareth 2 (2) | 2.3 |
| Sunflower seed oil (3) | 2.0 |
| Fragrance | 1.0 |

Example 3 also proved to be a highly efficacious antiperspirant composition, giving a significantly greater SWR than Comparative Example A (p<0.0001) in a head-to-head test as previously described.

The invention claimed is:

1. A process for the manufacture of an aqueous antiperspirant composition comprising the steps of: (i) mixing a basic aluminium chloride salt, water soluble calcium salt, amino acid, and water, (ii) heating the mixture to a temperature of greater than 110° C. at a pressure of 3 Bar (3,000,000 Pa) to 7 Bar (700,000 Pa) and (iii) restoring the mixture to ambient temperature and pressure, wherein the basic aluminium chloride salt is aluminium sesquichlorohydrate of the formula $Al_2OH_{4.4}Cl_{1.6}$ to $Al_2OH_{4.9}Cl_{1.1}$, wherein the process is carried out using ultra-high temperature (UHT) processing equipment.

2. The process according to claim 1, wherein the amino acid is glycine.

3. The process according to claim 1, wherein the molar ratio of calcium to aluminium is from 1:20 to 1:2 and the molar ratio of amino acid to aluminium is from 1:10 to 1:1.

4. The process according to claim 2, wherein the basic aluminium chloride salt, water soluble calcium salt, amino acid, and water pass from a feed vessel into a first heat exchanger for heating the mixture to elevated temperature greater than 110° C., then into an insulated holding tube for keeping the mixture at the elevated temperature, then optionally into a second heat exchanger for cooling the mixture, the mixture finally being released through a pressure release valve and the mixture being pumped between the aforementioned heat exchangers by an electric pump.

5. The process according to claim 4, wherein the basic aluminium chloride salt, water soluble calcium salt, amino acid, and water are first pumped from the feed vessel into a homogeniser for thorough mixing prior to being pumped into the first heat exchanger.

6. The process according to claim 4, wherein the resulting resulting antiperspirant composition passes directly or indirectly into a further mixing vessel and is mixed with fragrance and emulsifier.

7. The process according to claim 1, wherein one or more additional components required for the formation of an antiperspirant roll-on composition is added to the mixture before the mixture is fully restored to ambient temperature.

8. The process according to claim 5, wherein additional water is added to the mixture in order to reduce its temperature.

9. The process according to claim 5, wherein fragrance and emulsifier are added to the mixture before the mixture is fully restored to ambient temperature.

10. The process according to claim 1, comprising the addition of an emulsifier system comprising a first emulsifier having an HLB value in the range of from 2 to 6.5 and a second emulsifier having an HLB value in the range of from 12 to 18 to the mixture.

11. A method of gaining an antiperspirancy benefit comprising the topical application to the surface of the human body of a composition prepared according to claim 1.

12. The process according to claim 1 wherein the basic aluminium chloride salt is employed at a concentration of from 1.4 to 5 $mol.dm^{-3}$.

13. The probe s according to claim 1 wherein the basic aluminium chloride salt is employed at a concentration of from 3 to 4.5 $mol.dm^{-3}$.

* * * * *